US009113998B2

(12) United States Patent
Romo

(10) Patent No.: US 9,113,998 B2
(45) Date of Patent: Aug. 25, 2015

(54) PATELLOFEMORAL DEVICE AND METHOD FOR USING THE SAME

(71) Applicant: Össur hf, Reykjavik (IS)

(72) Inventor: Harry Duane Romo, Aliso Viejo, CA (US)

(73) Assignee: OSSUR HF, Reykjavik (IS)

( * ) Notice: Subject to any disclaimer, the term of this patent is extended or adjusted under 35 U.S.C. 154(b) by 122 days.

(21) Appl. No.: 13/796,609

(22) Filed: Mar. 12, 2013

(65) Prior Publication Data

US 2013/0245523 A1 Sep. 19, 2013

Related U.S. Application Data

(60) Provisional application No. 61/610,020, filed on Mar. 13, 2012.

(51) Int. Cl.
*A61F 5/00* (2006.01)
*A61F 5/01* (2006.01)

(52) U.S. Cl.
CPC .............. *A61F 5/0125* (2013.01); *A61F 5/0123* (2013.01); *A61F 2005/0176* (2013.01)

(58) Field of Classification Search
CPC ....... A61F 5/01; A61F 5/0102; A61F 5/0123; A61F 2005/0132; A61F 2005/0134; A61F 2005/0137; A61F 2005/0141; A61F 2005/0155; A61F 2005/0158; A61F 2005/016
USPC .......... 602/5, 16, 23, 26, 27, 28, 29; 128/882, 128/891, 892
See application file for complete search history.

(56) References Cited

U.S. PATENT DOCUMENTS

| | | |
|---|---|---|
| 4,296,744 A | 10/1981 | Palumbo |
| 4,370,978 A | 2/1983 | Palumbo |
| 4,423,720 A | 1/1984 | Meier et al. |
| 4,425,912 A | 1/1984 | Harper |
| 4,445,505 A | 5/1984 | Labour et al. |
| 4,506,661 A | 3/1985 | Foster |
| 4,607,628 A | 8/1986 | Dashefsky |
| 5,002,045 A | 3/1991 | Spademan |
| 5,024,216 A | 6/1991 | Shiono |
| 5,277,697 A | 1/1994 | France et al. |
| 5,411,037 A | 5/1995 | Hess et al. |
| 5,417,646 A | 5/1995 | Gauvry |
| 5,554,105 A | 9/1996 | Taylor |

(Continued)

FOREIGN PATENT DOCUMENTS

EP 0 941 722 A1 9/1999

OTHER PUBLICATIONS

International Search Report from corresponding PCT Application No. PCT/US2013/030711 dated Jun. 12, 2013.

*Primary Examiner* — Michael Brown
(74) *Attorney, Agent, or Firm* — Workman Nydegger

(57) ABSTRACT

A patellofemoral brace or support has a main substrate, a hinge located on at least one of the lateral and medial sides, and a support system coupled to the main substrate and the hinge. The support system has a compression element removably securable over the main substrate and a cable having a first end anchored to a pivoting element connected to the hinge and a second end anchored to the compression element. The cable engages the hinge such that articulation of the hinge from an extension position to a flexion position pulls the compression element toward the hinge to exert a generally medial force over the main substrate.

20 Claims, 5 Drawing Sheets

(56) References Cited

U.S. PATENT DOCUMENTS

| | | | | |
|---|---|---|---|---|
| 5,599,288 | A | 2/1997 | Shirley et al. | |
| 5,613,943 | A | 3/1997 | Palumbo | |
| 5,759,167 | A | 6/1998 | Shields, Jr. et al. | |
| 5,797,864 | A * | 8/1998 | Taylor | 602/26 |
| 5,807,298 | A | 9/1998 | Palumbo | |
| 5,865,776 | A | 2/1999 | Springs | |
| 6,287,269 | B1 | 9/2001 | Osti et al. | |
| 6,436,066 | B1 | 8/2002 | Lockhart | |
| 6,551,264 | B1 * | 4/2003 | Cawley et al. | 602/16 |
| 7,004,919 | B2 | 2/2006 | Gaylord et al. | |
| 7,011,641 | B1 | 3/2006 | DeToro et al. | |
| 7,060,045 | B2 | 6/2006 | Mason et al. | |
| 7,083,586 | B2 | 8/2006 | Simmons et al. | |
| 7,198,610 | B2 | 4/2007 | Ingimundarson et al. | |
| 7,597,675 | B2 | 10/2009 | Ingimundarson et al. | |
| 7,662,122 | B2 | 2/2010 | Sterling | |
| 7,713,225 | B2 | 5/2010 | Ingimundarson et al. | |
| 7,749,181 | B2 * | 7/2010 | Simmons et al. | 602/23 |
| 7,794,418 | B2 | 9/2010 | Ingimundarson et al. | |
| 7,806,842 | B2 | 10/2010 | Stevenson et al. | |
| 7,819,830 | B2 | 10/2010 | Sindel et al. | |
| 7,862,528 | B2 | 1/2011 | Scott | |
| 7,867,183 | B2 | 1/2011 | Kazmierczak et al. | |
| 7,896,827 | B2 | 3/2011 | Ingimundarson et al. | |
| 7,959,590 | B2 | 6/2011 | Scott | |
| 2002/0133108 | A1 | 9/2002 | Jagodzinski | |
| 2003/0204156 | A1 | 10/2003 | Nelson et al. | |
| 2004/0054307 | A1 * | 3/2004 | Mason et al. | 602/16 |
| 2004/0176715 | A1 | 9/2004 | Nelson | |
| 2005/0004499 | A1 * | 1/2005 | Bauerfeind et al. | 602/26 |
| 2008/0139985 | A1 * | 6/2008 | Gilmour | 602/26 |
| 2009/0131844 | A1 | 5/2009 | Dean et al. | |
| 2011/0098618 | A1 | 4/2011 | Fleming | |
| 2011/0137220 | A1 * | 6/2011 | Vollbrecht et al. | 602/16 |
| 2013/0172797 | A1 * | 7/2013 | Merkley et al. | 602/16 |

* cited by examiner

PATELLOFEMORAL DEVICE AND METHOD FOR USING THE SAME

FIELD OF ART

The present disclosure relates to the field of orthopedic devices, and more particularly to a patellofemoral device and method for using the same for supporting a patella.

BACKGROUND

There are numerous orthopedic devices such as braces that provide support around a patella of a user. Many of these braces use a stationary or static buttress that provides support about the patella of the user.

Some of the known braces include a front central opening that allow for the wearer's patella or kneecap to project therethrough. The front central opening relieves pressure otherwise exerted on the patella, particularly when the knee is bent or in flexion. These braces may include a pad or buttress located about the front central opening to provide a restraining force to the patella and additional support for preventing lateral or medial displacement of the patella in the femoral groove.

Despite known solutions, many braces fail to maintain the patella pad in a proper position on the support so the opening or pad can prevent patella displacement.

Alternatively, another example of a brace has a strap and a patella buttress attached to the strap for applying patellar support. One end of the strap has the patella buttress fixed near the patella of a user and a second end secures to a connection point along a lateral or medial side of the brace. As the strap is tensioned, the buttress applies pressure about the patella.

Despite known solutions, many devices fail to maintain the patella pad in a proper position on the support so the opening or pad can prevent patella displacement. Therefore, there is a need for a knee brace that at least provides means for stabilizing and supporting the patella.

SUMMARY

The present disclosure is directed to a patellofemoral device and method for using the same for supporting a patella. The embodiments and method described provide ample support against patellar subluxation during flexion and extension of a knee. An example of the patellofemoral device is a knee brace that provides suitable pressure around a patella of the knee during flexion.

In an embodiment of the patellofemoral device, a knee brace has a main substrate, such as a tubular support, panel or frame, and a patella support system. The main substrate defines lateral and medial sides and is adapted to secure about a knee, such as on the upper and lower leg portions adjacent the knee of a wearer. A hinge is located on at least one of the lateral and medial sides.

A support system is coupled to the main substrate and the hinge. The support system includes a compression element removably securable over the main substrate and a cable having a first end anchored to a pivoting element connected to the hinge or a strut extending from the hinge, and a second end anchored to the compression element. The cable engages the hinge such that articulation of the hinge from an extension position to a flexion position pulls the compression element toward the hinge to exert a generally lateral force over the main substrate.

The support system may include a guide connected to the hinge and arranged to route the cable from the pivoting element relative to the compression element. The guide may route the cable in a generally perpendicular orientation from the pivoting element to the compression element when the orthopedic device is in an extension configuration. For example, the cable may extend laterally from the hinge, and the guide may be located on the hinge and channel the cable in a perpendicular orientation from the pivoting element to a lateral location over the main substrate. The cable may be arranged to slide through the guide as the hinge articulates from extension to flexion.

Upper and lower struts may extend from the hinge and connect to the main substrate in a longitudinal direction, with the hinge articulating relative to the upper or lower strut.

The pivoting element may be located on a portion of the hinge secured to one of the struts and is arranged move generally uniformly with the strut upon which it is attached. The pivoting element may be a fastener, hook, or other support mounted on the corresponding strut.

The main substrate preferably defines a central opening about which the compression element secures. The orthopedic device may also include a buttress arranged to secure along a surface of the main substrate about the central opening. The buttress is preferably securable about the central opening of the main substrate, and may be oriented in a laterally opposing manner. The hinge may be generally laterally aligned with the opening. The device may include a pair of circumferential straps extending above and below the hinge and outside of the central opening.

The device includes a patellar flap extending from a side on the main substrate opposite the side on which the first end of the cable is located. The patellar flap is removably securable over the main substrate and counteracts with the compression element. The patellar flap may be flexible and elastic, and the compression element is preferably inelastic. The compression element may be securable over the patellar flap, and may be semi-rigid or rigid, and defines a central opening.

Referring to a method for using the aforementioned device, the method includes the steps of placing the hinge device in an extension configuration, extending the cable over a guide on the hinge device at a second location with the first location being spaced apart from the second location, positioning and securing the compression element over the main substrate; and flexing the hinge device and extending the length between the first and second locations, such that the cable incurs a laterally or medially directed force over the main substrate corresponding to the compression element.

From the patellofemoral device and method for using the same, the patella has increased support against patellar subluxation and causes pain by generating an increased amount of lateral or medial tension around the patella during knee flexion.

The patella support system may be provided as a kit and is secured to hinge components of a brace, and the compression element is attachable to a panel, substrate or frame. A supplementary panel or substrate, for example a tubular support about the knee in supplement to a rigid frame attaching to the upper and lower leg portions of a wearer, may be provided in combination with the patella support system for attachment to a frame and securing at least about a portion of a surface of a knee.

The numerous advantages, features and functions of the embodiments will become readily apparent and better understood in view of the following description and accompanying drawings. The following description is not intended to limit the scope of the orthopedic device, but instead merely provides exemplary embodiments for ease of understanding.

Figure 1:
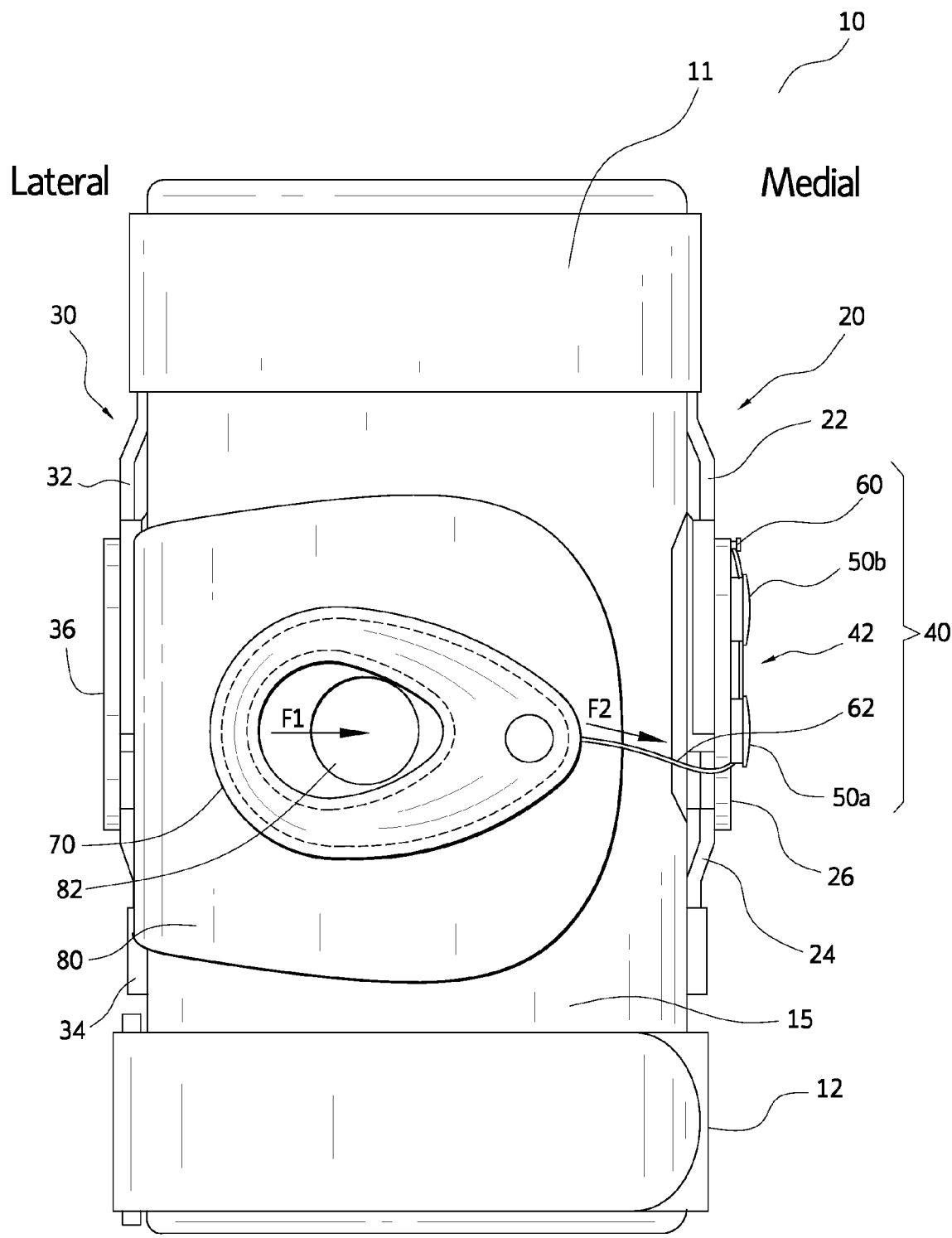
FIG. 1 shows a front view of an embodiment of a knee brace having a patella support system.

In the various figures, similar elements are provided with similar reference numbers. The drawing figures are not necessarily drawn to scale, or proportion, but instead are drawn to provide a better understanding of the components, and are not intended to be limiting in scope, but rather to provide exemplary illustrations.

DETAILED DESCRIPTION OF VARIOUS EMBODIMENTS

A. Overview of the Patella

The patella is a flat triangularly shaped bone having articular surfaces with medial and lateral facets. Given the uneven shapes of the articular surfaces, the patellofemoral joint formed between the patella and the femur is mostly incongruent and the stability of the patella depends on static and dynamic structures of the patella and femur.

In view of the incongruence of the patella, the contact between the patella and the femur changes throughout the knee range of motion (ROM). When the patella sits in the femoral sulcus in the extended knee, only the inferior pole of the patella contacts the femur. As the knee flexes, the patella slides down the femur, increasing the surface contact area. The contact area increases and shifts from the initial inferior location on the patella to a more superior position when the tibiofemoral flexion progresses. The contact area shifts superiorly along the posterior aspect of the patella, and spreads outward to cover the medial and lateral facet. At full flexion, the patella is lodged in the intercondylar groove.

Contact between the patella and femur changes throughout the range of motion of the knee, and the patella simultaneously translates and rotates on the femoral condyles. The patella is pulled down and under the femoral condyles when the knee flexes, ending with the apex of the patella pointing posteriorly in full flexion. Knee extension brings the patella back to its original position in the femoral sulcus, with the apex of the patella pointing inferiorly at the end of the normal ROM.

As is well understood, extension is defined as the straightening movement that increases the angle between body parts. For example, when a person is standing up, the knees are extended or in extension. Flexion is the opposite of extension and occurs when movement decreases the angle between two parts, such as when a person bends a knee.

During flexion and extension, the patella rotates around a longitudinal, or nearly vertical, axis and tilts around an anteroposterior axis. When the tibia medially rotates beneath the femur during axial rotation, the patella must remain in the intercondylar groove during the relative lateral rotation of the femur. This lateral rotation correspondingly forces the patella to face more laterally outward.

Rotation of the patella about an anteroposterior axis, such as medial or lateral rotation of the patella, is necessary for the patella to remain seated between the femoral condyles as the femur undergoes axial rotation relative to the tibia. When the knee undergoes some flexion and there is medial rotation of the tibia relative to the femur, the inferior pole of the patella will point medially outward, thus resulting in medial rotation of the patella. In lateral rotation of the patella, the inferior patellar pole follows the laterally rotated tibia.

The patella undergoes translational motions that depend on the point in the tibiofemoral ROM. The patella translates superiorly and inferiorly with knee extension and flexion, respectively. In particular, the patella glides superiorly during active extension. However, restricting this glide compromises the function of the quadriceps, and passive knee extension may be lost. During active tibiofemoral flexion, the patella glides inferiorly and can limit knee flexion.

A medial-lateral translation of the patella occurs simultaneously with the knee flexion that accompanies the superior-inferior glide. The patella is typically located slightly laterally in the femoral sulcus with the knee in full extension; as the knee flexion is initiated, the patella shifts medially. As knee flexion proceeds past 30°, the patella may shift slightly laterally or remain fairly stable and engage the femoral condyles. The patella shifts as the knee moves from full extension into flexion. Failure of the patella to slide, tilt, rotate, or shift appropriately can lead to restrictions in knee joint ROM, instability of the patellofemoral joint, or pain caused by erosion of the patellofemoral articular surfaces.

In the extended knee, instability can be a problem because the patella sits on the shallow aspect of the superior femoral sulcus where there is less bony stability and less patellofemoral compression from the quadriceps. As knee flexion is initiated to about 20°, the patella begins to slide down the femur and into the femoral sulcus, which increases medial-lateral stability by adding the bony stability of the femoral sulcus.

The longitudinal stabilizers of the patella comprise the patellar tendon inferiorly and the quadriceps tendon superiorly. The longitudinal stabilizers can provide medial-lateral stability of the patella in knee flexion through increased patellofemoral compression.

The transverse stabilizers are composed of the superficial portion of the extensor retinaculum. This retinaculum connects the vastus medialis and vastus lateralis muscles directly to the patella for improved muscular stabilization. The thickest portion of the medial retinaculum provides approximately 60% of the passive restraining force against lateral translation, i.e., lateral shift, of the patella.

The passive mobility of the patella and its medial-lateral positioning are largely governed by the passive and dynamic pulls of the structures surrounding it. The presence of hypermobility can cause patellar subluxations or dislocations. A relative weakness of the vastus medialis muscle may substantially increase the resultant lateral forces on the patella.

In view of the forces that act on the patella during knee flexion, the present embodiments of a brace having a patella support system are arranged to support relatively weak muscles and tendons during knee flexion for maintaining proper tracking of the patella in the underlying trochlear groove.

B. Various Embodiments of the Patellofemoral Device and Method for Using the Same As discussed above, the tracking of the natural movement of the patella during knee flexion can cause subluxation and discomfort to the user. Such problems associated with improper tracking may be prevented by using the patellofemoral device of the present invention and the method for using the same to provide patella support to a user.

In an embodiment of the patellofemoral device, a knee brace includes a first hinge 26 connected to upper and lower arms 22, 24 of a medial strut 20, and a patella support system 40 including a cable tightening system 42 having a cable 62, and a compression element 70 connected to the cable 62. The compression element 70 is removably attachable around the patella of the wearer on a main substrate 15 provided alone or in supplement to a brace frame such as rigid or semi-rigid types known in the art of knee bracing. The cable tightening system 42 includes guide members 56 used to guide and permit tensioning of the cable 62 so that stabilizing pressure is provided about the patella of the wearer during knee flexion.

FIG. 1 shows a knee brace 10 configured to maintain proper tracking of the patella in the underlying trochelar groove of the wearer during movement of the knee. The brace 10 has a main substrate 15, such as a flexible sleeve, formed from a tubular soft-good sleeve body. In this embodiment, the tubular nature of the main substrate allows for the pulling up of the sleeve to surround the upper and lower leg of a user and to provide compressive forces about the knee. Additionally, a central opening or patellar opening 82 is preferably formed in the main substrate to align with the wearer's patella.

The main substrate 15 can also be a flat panel configured to wrap around the knee of the wearer and fastened using straps, attaching members, or other fastening devices. The panel is segmented to surround or cover a portion of the circumference of the leg and/or knee. The brace 10 may preferably include a semi-rigid or rigid frame for providing additional support and protection around the knee of the wearer. The panel may be in combination with the frame, and attached thereto by suitable straps in order to at least cover part of an anterior aspect of the knee to allow for placement of the compression element 70 thereon.

According to the depicted embodiment, the brace 10 is adapted to provide pressure around the patella of the wearer by applying laterally tensioned forces thereto. It will be understood that the patella support system 40 can further be arranged on opposite lateral sides of the brace to provide laterally tensioned forces and pressure around the patella of the wearer.

The brace 10 has the medial strut 20 and a lateral strut 30 coupled to the main substrate 15 for providing additional support and a customized fit when the knee is flexed. The medial strut 20 includes upper and lower arms 22, 24 connected by a first hinge 26, while the lateral strut 30 includes upper and lower arms 32, 34 connected by a second hinge 36. The hinges and arms can be made of metal, plastic, or other hard material for providing added stability around the lateral and medial sides of the knee.

Circumferential straps 11, 12 are provided to secure the brace 10 to the leg of the wearer and prevent rotation of the brace during movement. The circumferential straps 11, 12 are formed from an elastic or non-elastic material, such as neoprene, foam, nylon or other flexible textile. The circumferential straps may also provide a compressive force around the knee. The circumferential straps 11, 12 may be attached to the brace 10 by buckles, hook and loop fasteners, buttons, pins, or other fastening mechanisms that allow the tightening and securing of the circumferential straps around the leg of the wearer.

The first hinge 26 rotationally connects the medial upper arm 22 and the medial lower arm 24 about a first pivot point. The first hinge 26 can be any hinge well known in the art that allows for rotation between the medial upper and lower arms 22, 24. The first hinge 26 may be a polycentric hinge or other articulated knee supporting hinge, such as a drop lock or ROM hinge, allowing the medial upper and lower arms 22, 24 to rotate. The rotation of the medial upper and lower arms 22, 24 can be provided, for example, by using intermeshing teeth on the upper and lower arms or by pivotally connecting the ends of the medial upper and lower arms 22, 24 using a pin to enable the rotation.

The first hinge 26 couples to a patella support system 40 arranged to generate medially tensioned forces and pressure around the patella of the wearer to provide proper tracking of the patella of the wearer during knee flexion. The patella support system 40 includes a cable tightening system 42 having at least a first guide member 50a and a second guide member 50b, and a cable 62 that runs through the at least two guide members 50a, 50b. The cable 62 has a first end coupled to a compression element 70 and a second end coupled to a patella support system a pivoting element 60, such as a pin, screw or other fastener.

The pivoting element 60 may comprise a portion of the hinge or the strut, and functionally retains a first end of the cable relative to the strut as the hinge or hinge components articulate relative to the strut. The cable 62 may be made from an elastic or non-elastic material, steel, braided steel or polymer, plastic, neoprene, wire, or similar material. Preferably, the cable 62 is non-elastic to provide the proper tensioning forces and pressure to maintain patellar tracking during knee flexion.

Figure 2:
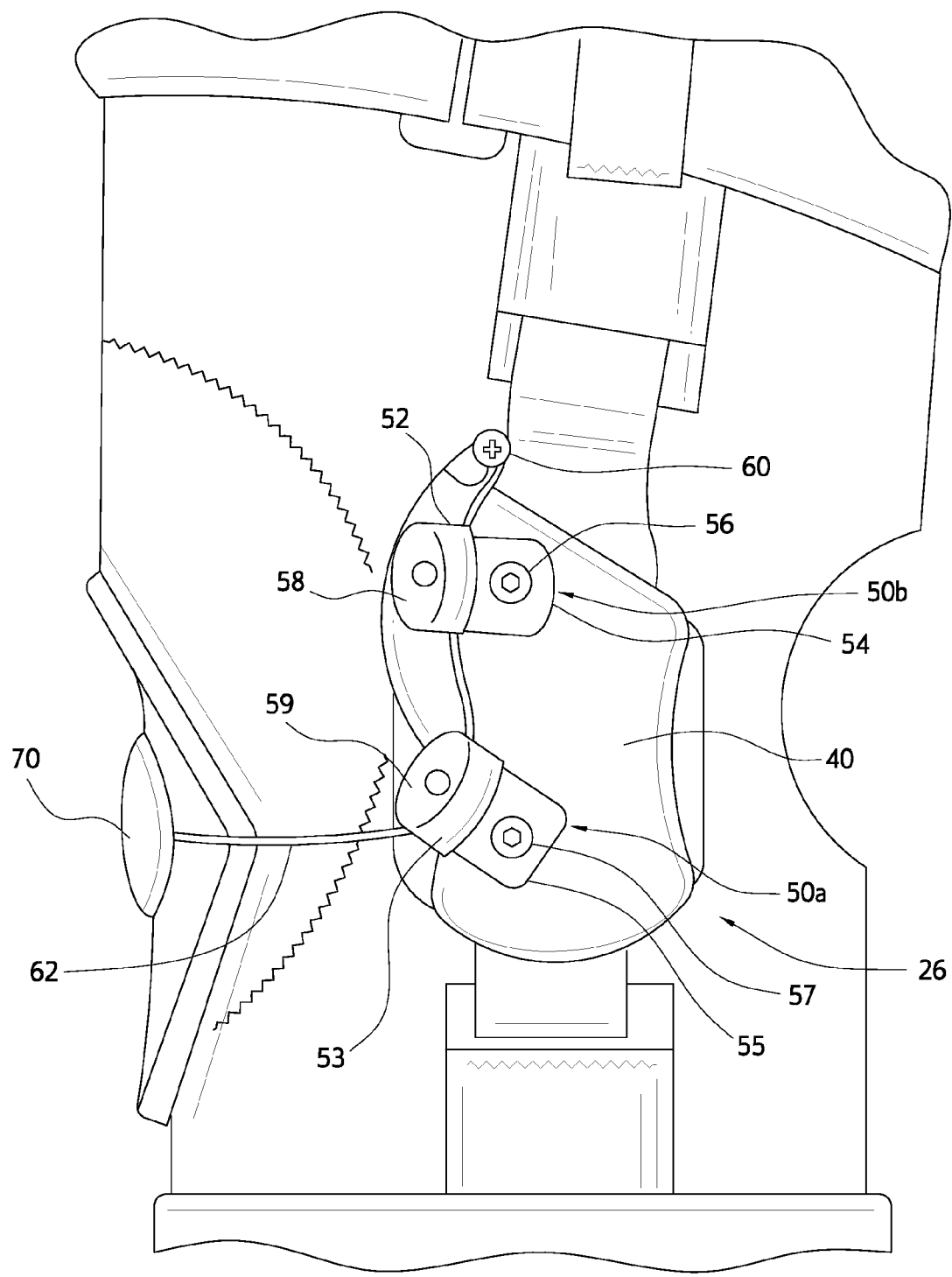
FIG. 2 shows a lateral side view of the knee brace of FIG. 1 in extension.

As seen in FIG. 2, the guide members 50a, 50b are secured to the first hinge 26 by tab sections 54, 55 attached to the first hinge 26 via fastening members 56, 57, such as rivets or screws. In this embodiment, the guide members 50a, 50b are pivotally mounted on the hinge 26 to allow for movement of the guide members during flexion and extension of the knee. Alternatively, the guide members 50a, 50b can instead be firmly mounted in a fixed position on the first hinge 26 to prevent movement of the guide members during flexion and extension of the knee in order to create additional tensioning force.

Guide members 50a, 50b permit movement of the cable 62 along an interior or exterior surface thereof, and can be guided through or along the guide members. In one embodiment, the cable is adapted to move along an inner surface of guiding sections 58, 59 connected to the tab sections 54, 55. The guiding sections 58, 59 form inner passageways 52, 53 along their respective internal surfaces.

The inner passageways 52, 53 may be formed during the manufacturing of the guiding sections 58, 59 by creating a ridge in each guiding member such that the inner passageways 52, 53 are formed when the guiding sections 58, 59 are attached to the first hinge 26. Alternatively, the inner passageways can be bored through the guide members 50a, 50b after manufacturing, or formed as a lip (not shown) or other structure arranged to prevent the cable 62 from slipping away from the guide members 50a, 50b during movement of the cable. It should further be appreciated that the passageways 52, 53 may be formed along either an interior or exterior surface of the guiding members.

The cable 62 has a first end connected to a compression element 70 and a second end coupled to a pivoting element 60. The first end of the cable 62 can be attached to the compression element 70 by stitching, welding, bonding, or other well known attaching means. FIG. 2 shows that the cable 62 runs from the compression element 70 along the inner passageway 52 of the first guide member 50a and then along the inner passageways 52, 53 of the second guide member 50b. FIG. 2 shows the second end of the cable 62 as being coupled to the pivoting element 60 by a screw, rivet, or other fastening element, or by gluing, welding, or bonding.

Figure 3:
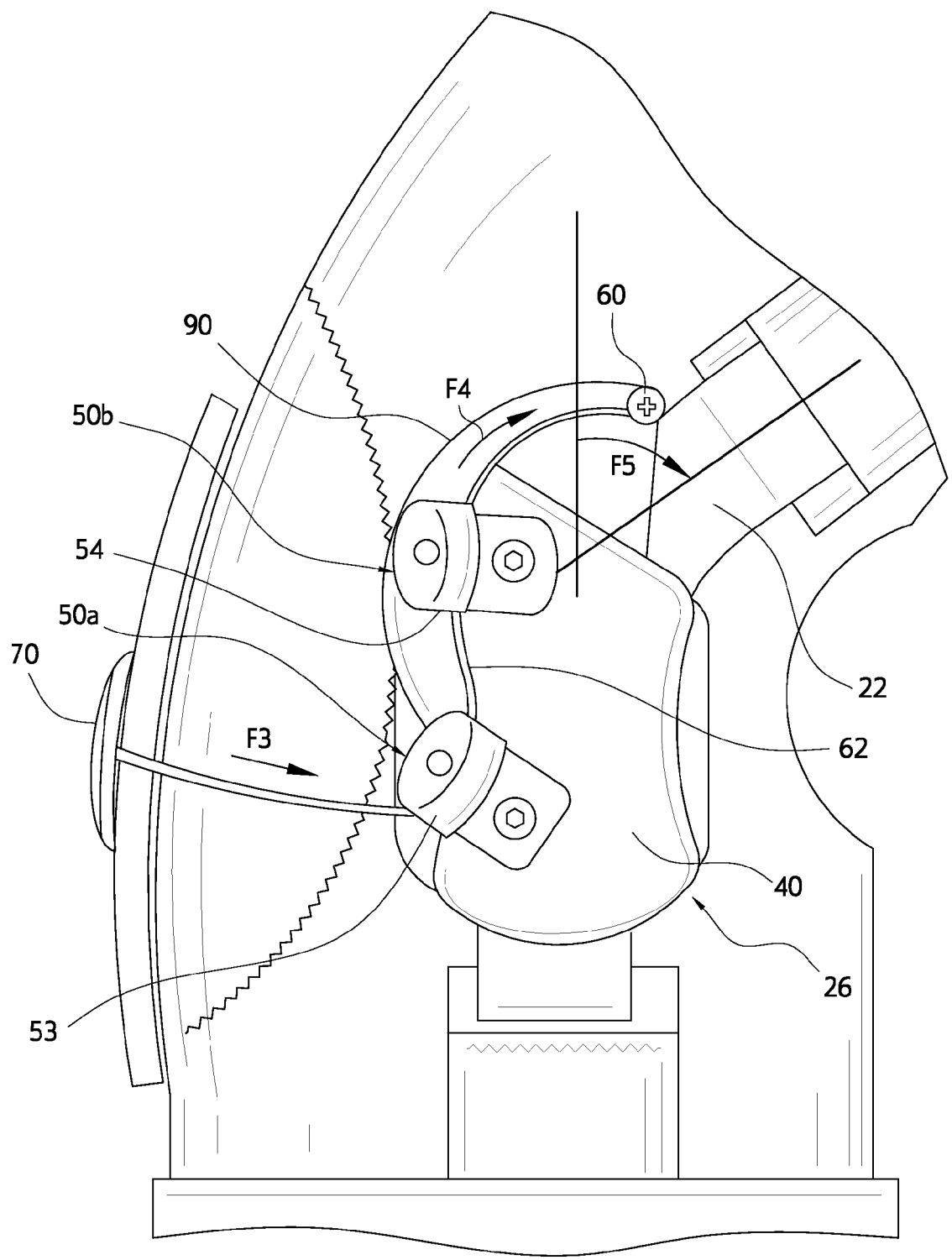
FIG. 3 shows a lateral side view of the knee brace of FIG. 1 in flexion.

FIG. 3 illustrates the tightening of the cable 62 by the patella support system 40 as using the pivoting element 60. The pivoting element 60 creates tension in the cable 62 by using a pivoting plate 90 pivotally attached to the patella support system 40 and coupled to the upper arm 22.

The tensioning force can be adjusted by lengthening or shortening the cable 62 by using a reeled spool, by cutting the cable, or using a device that allows for lengthening or shortening of the cable. Additional guide members can be provided that are removably attachable to the patella support system to provide increased tension on the cable 62 during flexion or extension.

As seen in FIG. 3, the upper arm 22 of the medial strut 22 is rotationally connected to the ROM movements of the first hinge 26, which displaces the pivoting plate 90 from an inner housing (not shown) of the patella support system 40. When the hinge flexes, the cable 62 is tensioned by the movement of the pivoting element 60 since it is attached to the pivoting plate 90, and located away from the inner housing. The inner passageways 53, 54 of the corresponding guide sections provide a guiding direction for the cable 62 during tensioning so that tension can be applied to the compression element 70 attached around the patella of the wearer.

Alternatively, the second end of the cable 62 can be directly attached to the upper arm 22 to allow 62 the guiding members 58, 59 to tighten the cable 62 during flexion movement of the first hinge 26.

A compression element 70 may be coupled to the first end of the cable 62, and is removably coupled near a patellar opening 82 using a fastener such as hook and loop fasteners, pins, button, or other fastening members to secure the compression element 70 to the brace 10. In particular, the compression element 70 may be permanently attached near the patellar opening 82 where the first end of the cable 62 is attachable to the compression element 70 by the fastener.

The compression element 70 may be rigid or semi-rigid so as to more firmly apply lateral pressure over the patella as the cable is tensioned. According to this embodiment, the compression element is inelastic so as to maintain its shape as the cable is tensioned and the compression element exerts pressure over the patella. Alternatively, the compression element may be flexible and resilient so as to conform to the shape of a wearer's leg while having sufficient resiliency to withstand the lateral pulling caused by the cable.

A patellar flap 80 can be used with the compression element 70 to provide additional security and support to the wearer's knee. The patellar flap 80 may include a patella buttress (not shown) that abuts the patella of the wearer near the patellar opening 82, and may be in the form of a U-shape, C-shape, J-shape or any other similarly shaped configuration capable of wrapping around a portion of the patella. The patella buttress can also be attached on the internal or external surface of the patellar flap 80, or alternatively be integrated inside the patellar flap 80. Additionally, the patella buttress may constitute padding about the patellar opening, or comprise both the padding and a removable buttress.

Figure 4:
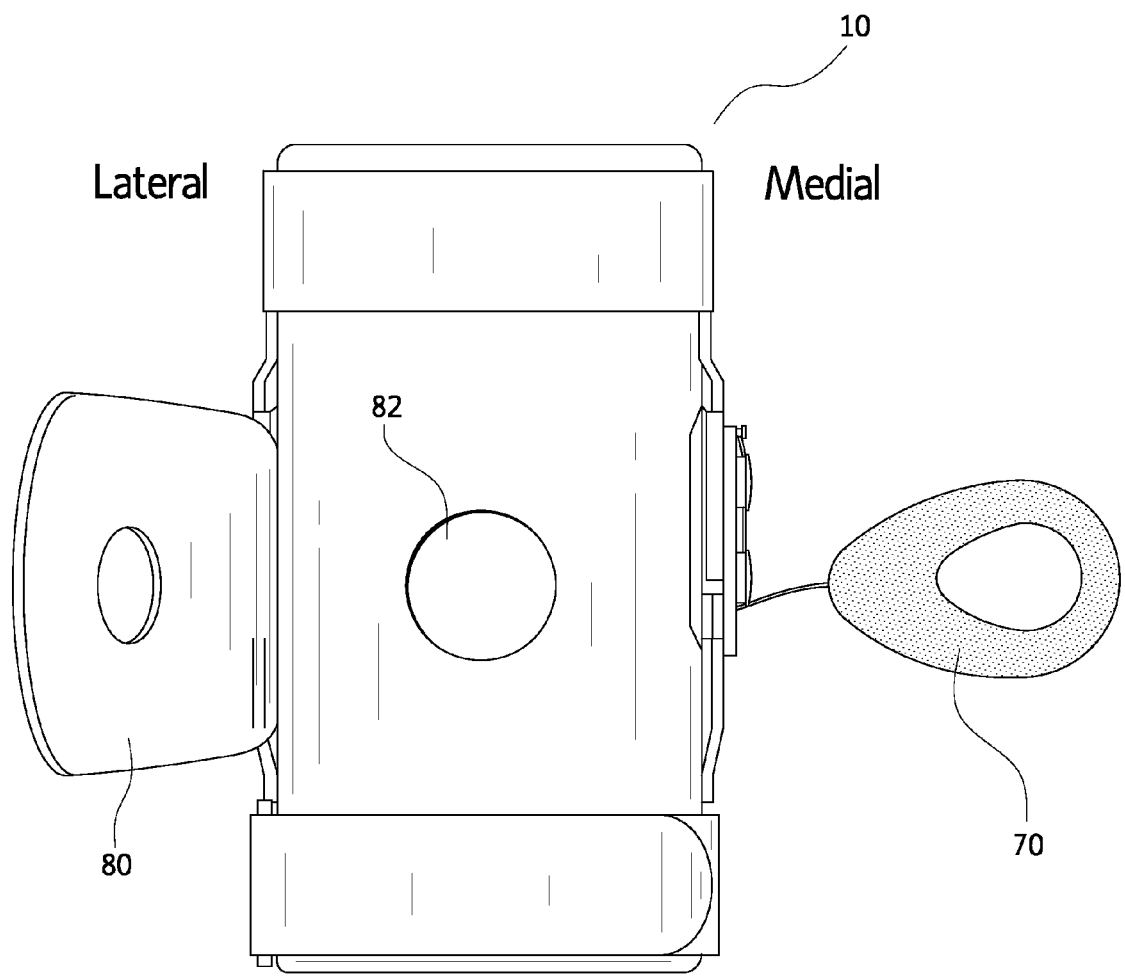
FIG. 4 shows a perspective view of the knee brace of FIG. 1 with a patella support system at least partially disengaged from a main substrate.

As seen in FIG. 4, the patellar flap 80 can be attached near the medial side of the brace 10 such that the patellar flap 80 overlies the patellar opening 82. Accordingly, if the brace 10 includes the patellar flap 80, then the compression element 70 is preferably configured to attach to an external surface of the patellar flap 80 using a fastener.

The patellar flap 80 and the compression element 70 are preferably arranged so as to be applied in counteracting directions. For example, if the patellar flap 80 extends from the medial side, then the compression element 70 extends from the lateral side. It should be appreciated that the compression element 70 can alternatively be arranged on the brace to extend from the medial side for engagement with the patellar flap 80 configured to extend form the medial side.

Figure 5:
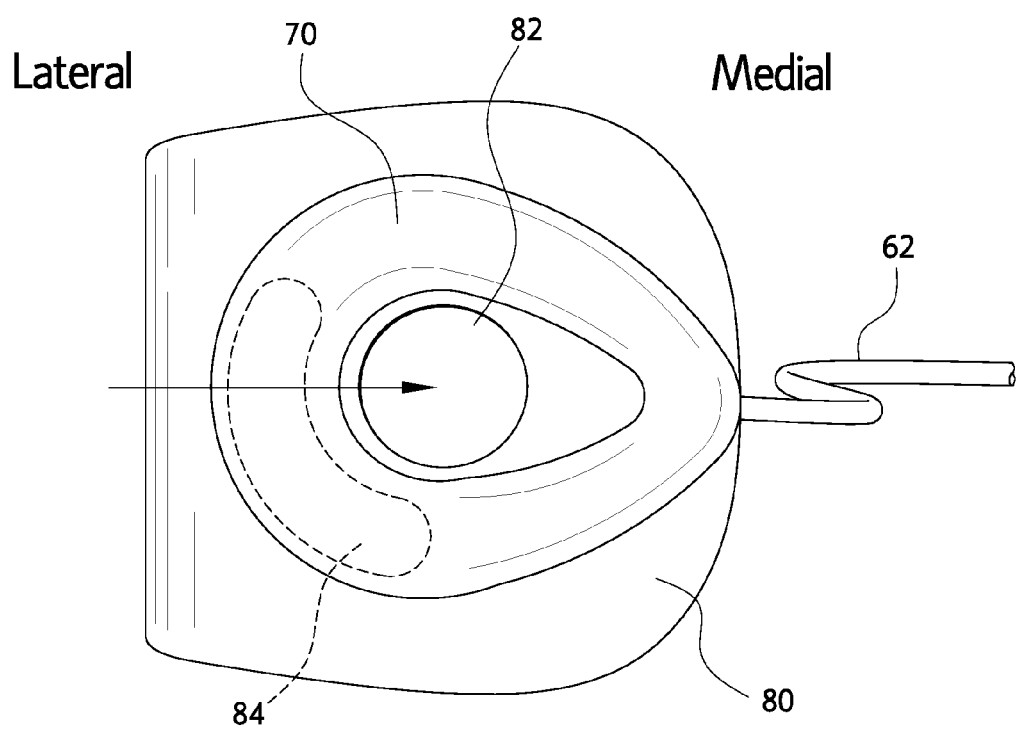
FIG. 5 is a schematic view of another embodiment of a patella support system.

FIG. 5 illustrates an embodiment of the patellar flap 80 made of a flexible and elastic material to allow the maximum loading during knee flexion. The patellar flap may include a patella buttress 84 configured to laterally restrict the movement of the patella during knee flexion and load the patellar tendon. The patella buttress 84 can have the form of a J-shaped buttress, U-shaped buttress, C-shaped buttress, or can be custom fitted to apply the desired force to the patella of the wearer.

The patella buttress may be arranged in a laterally opposing manner relative to the compression element. For example, as depicted in FIG. 5, the patella buttress 84 has a U-shape that corrals a medial side of the patella whereas the cable and compression element extend from the lateral side so as to pull the buttress laterally.

The patellar flap 80 can be directly attached to the brace 10 around the patellar opening 82 using hook and loop material, buttons, straps, snap fittings or other well known fastening devices for the securement of the patellar flap 80.

The compression element 70 and the patellar flap 80 preferably define an opening arranged to generally correspond to the patellar opening 82 formed in the main substrate. Although both include an opening, it is not essential that the openings of the compression element and the patellar flap correspond exactly on one another, however the compression element is arranged to secure over the patellar flap.

In a method for using the patellofemoral brace or support may include the steps of placing the hinge device in an extension configuration, extending the cable over a guide on the hinge device at a second location with the first location being spaced apart from the second location, positioning and securing the compression element over the main substrate; and flexing the hinge device and extending the length between the first and second locations, such that the cable incurs a laterally or medially directed force over the main substrate corresponding to the compression element.

According to the embodiments described, the patella support system may be provided as a kit securable to hinge components of a brace, and the compression element is securable to a panel, substrate or frame. A supplementary panel or substrate, for example a tubular support about the knee in supplement to a rigid frame attaching to the upper and lower leg portions of a wearer, may be in combination with the patella support system for attachment to a frame and securing at least about a portion of a surface of a knee.

C. Biomechanics of the Patella Support System

The patella support system is described as being arranged to create medially directed forces and pressure around the patella of the wearer of the brace 10 during knee flexion. The forces are created by the tensioning of the cable 62 connected to the compression element 70 and securely attached around the patella of the wearer and the patella support system 40.

When the first hinge 26 enters a flexion motion, the pivoting element 60 tensions the cable 62 by pivoting from the inner housing. The pulling of the second end of the cable 62 provides a medial pulling force at the first end of the cable 62 around the patella of the wearer by pulling on the compression element 70.

The medially directed tensioning force allows for proper tracking of the patella of the wearer in the intercondylar grooves to prevent subluxation, dislocations, and/or improper patellar tracking. By providing a medially directed force, the pressure applied by the compression element 70 helps support weak tendons and muscles, and prevents errant movements of the patella of the wearer during different motions of the knee.

Different tensioning forces are created during knee extension, based on the pulling of the second end of the cable 62. As the wearer of the brace 10 starts knee flexion, a small amount of medially directed force is generated. As the second end of the cable is pulled further by the pivoting element 60, a greater amount of medially directed tensioning force is created.

Although the description above refers to a patella support system for providing a medially directed tensioning force to the patella, the patella support system can also be configured to provide a laterally directed force around the patella of the wearer to prevent patellar subluxation.

While the foregoing embodiments have been described and shown, alternatives and modifications of these embodiments, such as those suggested by others may be made to fall within the scope of the disclosure. Any of the principles described may be extended to any other orthopedic devices, prosthetic devices or other types of articles requiring similar functions of those structural elements described.

The foregoing elements are not limited to use in a knee brace, but can also be used in an arm brace or similar device that requires providing a tensioning force on a body part during flexion or extension. The patella support system can further be adapted to support an elbow in the form of an elbow support system. Since one end of the cable is connected to a compression element securely attached around the elbow of the wearer and the second end is connected to a pivoting element used to pull the cable, when the arm is bent, the elbow support system tensions the cable connected to the compression element.

The invention claimed is:

1. An orthopedic device defining lateral and medial sides, comprising:
   a main substrate;
   a hinge located on at least one of the lateral and medial sides;
   a medial strut having first and second arms located on opposed sides of the hinge, the first arm articulating relative to the hinge;
   a support system coupled to the main substrate and the hinge, the support system comprising a compression element arranged to extend around a patella and having a fastener removably securable to a surface of the main substrate and a non-elastic cable having a first end anchored to a pivoting element secured to the upper arm to retain the first end of the cable to the first arm as the hinge articulates, and a second end anchored to the compression element, the cable engaging the hinge such that articulation of the hinge from an extension position to a flexion position pulls the compression element toward the hinge to exert a generally lateral force over the main substrate;
   wherein a first guide is mounted on the hinge and arranged to route the cable from the pivoting element relative to the compression element.

2. The orthopedic device of claim 1, wherein a single cable secures to the hinge and compression element.

3. The orthopedic device of claim 2, wherein the first guide routes the cable in a generally perpendicular orientation from the pivoting element to the compression element when the orthopedic device is in an extension configuration.

4. The orthopedic device of claim 1, wherein the first arm is located above the hinge.

5. The orthopedic device of claim 4, wherein the pivoting element is located on a pivoting plate secured to the first arm and arranged to move generally uniformly with the first arm from an inner housing of the hinge.

6. The orthopedic device of claim 5, further comprising a patella buttress securable about a central opening of the main substrate, and oriented in a laterally opposing manner.

7. The orthopedic device of claim 1, wherein the compression element is semi-rigid or rigid, and defines a central opening.

8. The orthopedic device of claim 1, wherein the main substrate defines a central opening about which the compression element secures, the orthopedic device further comprising a buttress arranged to secure along a surface of the main substrate about the central opening.

9. The orthopedic device of claim 1, further comprising a patellar flap extending from a side on the main substrate opposite the side on which the first end of the cable is located, wherein the patellar flap is removably securable over the main substrate and counteracts with the compression element.

10. The orthopedic device of claim 9, wherein the patellar flap is flexible and elastic, and the compression element is inelastic.

11. The orthopedic device of claim 9, wherein the compression element is securable over the patellar flap.

12. The orthopedic device of claim 1, further comprising a patella buttress securable about a central opening of the main substrate, and oriented in a medially opposing manner.

13. The orthopedic device of claim 1, wherein the main substrate is a flexible sleeve having a central opening.

14. The orthopedic device of claim 13, further comprising a pair of circumferential straps extending above and below the hinge and outside of the central opening.

15. The orthopedic device of claim 13, wherein the hinge is generally laterally aligned with the opening, the first guide routing the cable in a generally perpendicular orientation from the pivoting element to the compression element when the orthopedic device is in an extension configuration such that the cable is laterally aligned from the first guide to the compression element with the opening.

16. The orthopedic device of claim 1, wherein the cable extends laterally from the hinge and the first guide to the compression element such that the first end terminates at the compression element on a medial side of the orthopedic device.

17. The orthopedic device of claim 1, wherein the pivoting element is a fastener mounted on the first arm.

18. An orthopedic device defining lateral and medial sides, comprising:
   a main substrate;
   a medial strut having first and second arms located on opposed sides of the hinge, the first arm articulating relative to the hinge;
   a support system coupled to the main substrate and the hinge, the support system comprising a compression element arranged to extend around a patella and having a fastener removably securable over to a surface of the main substrate and a non-elastic cable having a first end anchored to a pivoting element secured to the upper arm to retain the first end of the cable to the first arm as the hinge articulates, and a second end anchored to the compression element, the cable engaging the hinge such that articulation of the hinge from an extension position to a flexion position pulls the compression element toward the hinge to exert a generally lateral force over the main substrate;

a flexible and elastic patellar flap extending from a side on the main substrate opposite the side on which the first end of the cable is located, wherein the patellar flap is removably securable over the main substrate and counteracts with the compression element.

19. An orthopedic device defining lateral and medial sides, comprising:
   a main tubular substrate;
   a hinge located on at least one of the lateral and medial sides;
   a medial strut having first and second arms located on opposed sides of the hinge, the first arm articulating relative to the hinge;
   a support system coupled to the main substrate and the hinge, the support system comprising a compression element arranged to extend around a patella and having a fastener removably securable to a surface of the main substrate and a single, non-elastic cable having a first end attached at and anchored to a pivoting element secured to the upper arm at a location generally adjacent the hinge in extension such that the pivoting elements retains the first end of the cable to the first arm as the hinge articulates, and a second end anchored to the compression element, the cable engaging the hinge such that articulation of the hinge from an extension position to a flexion position pulls the compression element toward the hinge to exert a generally lateral force over the main substrate;
   wherein a first guide is mounted on the hinge and arranged to route the cable from the pivoting element relative to the compression element in a generally perpendicular orientation when the hinge is in extension.

20. The orthopedic device of claim 19, wherein the hinge is generally laterally aligned with the opening and the hinge.

* * * * *